(12) United States Patent
Glaser

(10) Patent No.: US 10,258,727 B2
(45) Date of Patent: Apr. 16, 2019

(54) DISPOSABLE ARTICLES FOR DIALYSIS TREATMENT, DIALYZER AND A WATER PREPARATION PLANT FOR DIALYSATE

(71) Applicant: Fresenius Medical Care Deutschland GmbH, Bad Homburg (DE)

(72) Inventor: Benedict Glaser, Schweinfurt (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 211 days.

(21) Appl. No.: 14/913,694

(22) PCT Filed: Aug. 14, 2014

(86) PCT No.: PCT/EP2014/002246
§ 371 (c)(1),
(2) Date: Feb. 23, 2016

(87) PCT Pub. No.: WO2015/024647
PCT Pub. Date: Feb. 26, 2015

(65) Prior Publication Data
US 2016/0199559 A1    Jul. 14, 2016

(30) Foreign Application Priority Data
Aug. 23, 2013 (DE) .................. 10 2013 014 097

(51) Int. Cl.
*A61M 1/16* (2006.01)
*A61M 1/34* (2006.01)
(Continued)

(52) U.S. Cl.
CPC .......... *A61M 1/1656* (2013.01); *A61M 1/16* (2013.01); *A61M 1/1668* (2014.02);
(Continued)

(58) Field of Classification Search
CPC ............. A61M 1/1656; A61M 1/3659; A61M 1/1668; A61M 1/3621; A61M 1/3624;
(Continued)

(56) References Cited

U.S. PATENT DOCUMENTS

| 4,370,983 A * | 2/1983 | Lichtenstein ............ A61B 5/00 600/301 |
| 2002/0138067 A1* | 9/2002 | Sheppard, Jr. ........ A61K 9/0009 604/891.1 |

(Continued)

FOREIGN PATENT DOCUMENTS

| DE | 102008010948 | 9/2009 |
| DE | 102010038923 | 2/2012 |

(Continued)

*Primary Examiner* — Joseph W Drodge
(74) *Attorney, Agent, or Firm* — Jacobson Holman, PLLC.

(57) ABSTRACT

The invention relates to a disposable article for use in dialysis treatment which has at least one sensor for determining a measured value relating to the dialysis. The invention further relates to a dialyzer having a disposable article in accordance with the invention. The invention furthermore relates to a dialyzer and to a water preparation plant for dialysate having at least one sensor for determining at least one measured value relating to the dialysis, at least one transmitter which is connected to the sensor and is configured such that it enables a wireless transmission of the measured value to at least one receiver and at least one energy converter for providing energy, preferably electrical energy, to the sensor and to the transmitter.

12 Claims, 4 Drawing Sheets

Figure 1:
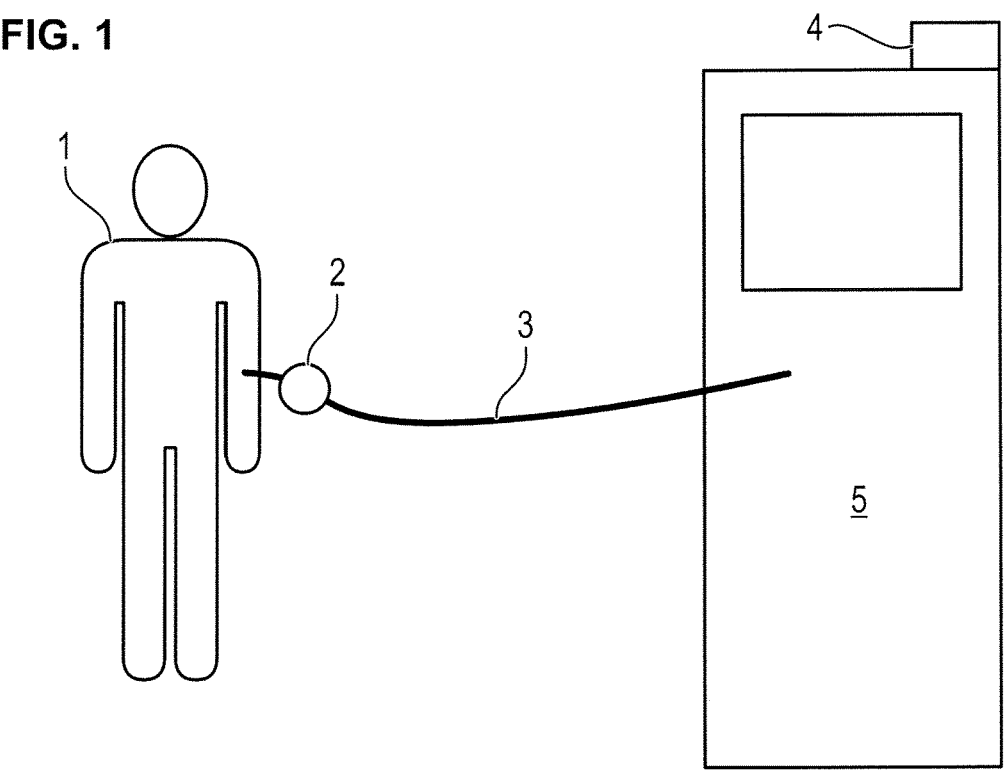

(51) Int. Cl.
*A61M 1/36* (2006.01)
*B01D 61/32* (2006.01)
*G01L 19/14* (2006.01)

(52) U.S. Cl.
CPC .......... *A61M 1/367* (2013.01); *A61M 1/3621* (2013.01); *A61M 1/3624* (2013.01); *A61M 1/3639* (2013.01); *A61M 1/3659* (2014.02); *B01D 61/32* (2013.01); *G01L 19/14* (2013.01); *A61M 2205/12* (2013.01); *A61M 2205/3331* (2013.01); *A61M 2205/3344* (2013.01); *A61M 2205/3368* (2013.01); *A61M 2205/3382* (2013.01); *A61M 2205/3386* (2013.01); *A61M 2205/3393* (2013.01); *A61M 2205/3569* (2013.01); *A61M 2205/3576* (2013.01); *A61M 2205/3592* (2013.01); *A61M 2205/702* (2013.01); *A61M 2205/82* (2013.01); *A61M 2205/8256* (2013.01)

(58) Field of Classification Search
CPC ...... A61M 1/3639; A61M 1/16; A61M 1/367; A61M 2205/3393; A61M 2205/3331; A61M 2205/702; A61M 2205/3368; A61M 2205/3386; A61M 2205/3382; A61M 2205/3344; A61M 2205/12; A61M 2205/3569; A61M 2205/3592; A61M 2205/82; A61M 2205/8256; A61M 2205/3576; A61M 1/1601; A61M 1/1603; A61M 1/1635; A61M 1/1647; A61M 1/34; A61M 1/342; A61M 1/3424; A61M 1/3427; A61M 1/3437; A61M 1/3462; A61M 1/3465; A61M 1/243; A61M 1/30; A61M 1/32; A61M 1/301; A61M 1/3406; A61M 1/341; A61M 1/36; A61M 1/3641; B01D 61/24; B01D 61/243; B01D 61/28; B01D 61/30; B01D 61/32; B01D 2311/14; B01D 2311/2603; B01D 2313/34; B01D 2313/36; B01D 2313/365; G01L 19/14; G01L 19/147; G01L 19/149

USPC ............ 210/90, 97, 137, 257.2, 258, 321.6, 210/321.71, 416.1, 637, 646, 647, 741; 604/4.01–6.11, 29–31, 65–67; 73/753, 73/756; 340/626
See application file for complete search history.

(56) References Cited

U.S. PATENT DOCUMENTS

| | | |
|---|---|---|
| 2007/0007184 A1 | 1/2007 | Voto et al. |
| 2009/0088683 A1 | 4/2009 | Roger et al. |
| 2009/0182392 A1* | 7/2009 | Woolaston ........... A61N 1/3785 607/57 |
| 2009/0204019 A1* | 8/2009 | Ginggen ................ A61B 5/031 600/561 |
| 2010/0140149 A1* | 6/2010 | Fulkerson ............... A61M 1/14 210/85 |
| 2011/0021887 A1* | 1/2011 | Crivelli ................ G01D 11/245 600/302 |
| 2011/0240555 A1* | 10/2011 | Ficheux ............... A61M 1/3413 210/637 |
| 2012/0175296 A1* | 7/2012 | Wehmeyer .......... A61M 1/1654 210/321.69 |
| 2012/0181231 A1* | 7/2012 | Beden ................ A61M 1/1037 210/646 |
| 2012/0297869 A1* | 11/2012 | Gagel ................... A61M 1/342 73/196 |
| 2012/0316799 A1 | 12/2012 | Gagel |
| 2013/0018301 A1* | 1/2013 | Weaver ............... A61M 1/3627 604/28 |
| 2013/0328416 A1* | 12/2013 | Whitworth ............. H02J 17/00 307/149 |

FOREIGN PATENT DOCUMENTS

| | | |
|---|---|---|
| WO | WO 01/89599 | 11/2001 |
| WO | WO 2005/077262 | 8/2005 |
| WO | WO 2009/153331 | 12/2009 |
| WO | WO 2010/108714 | 9/2010 |
| WO | WO 2011/079907 | 7/2011 |
| WO | WO 2012/095301 | 7/2012 |

\* cited by examiner

DISPOSABLE ARTICLES FOR DIALYSIS TREATMENT, DIALYZER AND A WATER PREPARATION PLANT FOR DIALYSATE

The invention relates to a disposable article for use in dialysis treatment and to a dialysis machine having such a disposable article.

A plurality of sensors are required at liquid-conducting lines in dialysis to ensure a reliable blood treatment. A plurality of state variables of the blood and of the treatment liquids are constantly registered during the dialysis treatment and the acquired data are evaluated in a processor unit. The temperature, the pressure, the liquid level, the conductivity, acoustic properties are in particular measured to be able to make a statement on the patient safety and in the event of doubt to trigger an alarm or a discontinuation of treatment.

As a rule, the blood in hemodialysis is conducted through an extracorporeal circuit which is designed as a disposable article. The extracorporeal circuit is made up of hose lines, filter modules, connectors, drip chambers and further elements. The sensors are parts of the treatment machine in previously known systems for dialysis treatment. They have to be brought into engagement with corresponding parts of the extracorporeal circuit so that measurements can be carried out. This makes the upgrading of the dialysis machine more difficult.

Furthermore, the current development aim is toward giving the extracorporeal circuit a more complex configuration. In the prior art, a number of blood treatment cassettes are described with which an attempt is more or less made to minimize the extracorporeal circuit to save material and resources. The sensor coupling between the dialysis machine and the extracorporeal circuit configured as a disposable is correspondingly made more difficult from a construction aspect due to the increasing complexity of the extracorporeal circuit.

Against this background, the invention proposes a disposable article for use in dialysis treatment which has at least one sensor for determining a measured value relating to the dialysis.

The term of a measured value relating to dialysis is to be given a wide interpretation within the framework of the present invention and includes all state variables or parameters of the dialysate or blood which can be measured anywhere in the disposable article. Preferred embodiments will be looked at a later point. The core subject matter of the invention is therefore that the disposable itself has a complete sensor and the respective sensor or a part of the sensor is therefore not arranged on the machine side. The upgrading of the dialysis machine is therefore facilitated and the measurement takes place directly and accurately, i.e. no potentially disturbing disposable is located between the sensor and the measurement medium of blood or dialysate.

In an embodiment, the disposable article furthermore has at least one transmitter which is configured so that it allows a preferably wireless transmission of the measured value to a receiver located outside the disposable article. Such systems can therefore transmit the measured signal to a receiver via radio. A number of advantages result. Among others, the measured data detection system is independent of location and a measured data detection is possible on the patient or at a site in the dialyzer having difficult access. The necessity of a cable can be dispensed with, which results in a simple assembly and a saving of construction space for a cable.

In an embodiment, the disposable article furthermore more has at least one energy converter for providing energy, preferably electrical energy. This use of technical systems for gaining energy from the environment is also known as energy harvesting. In dialysis technology, the available energy sources are, for example, the temperature difference between the dialysate or the blood and the environment (thermal energy) or pressure changes or movements, e.g. the pulsation or pressure change generated by a peristaltic pump (kinematic energy, mechanical energy). Furthermore, electromagnetic energy can be introduced, for example. This allows an autonomous operation of the sensor and/or of the transmitter and has the advantages over a battery or a rechargeable battery, for example, of possibly lower costs and lower space requirement. A battery or a rechargeable battery furthermore often contains poisonous substances which are problematic in the treatment and in the disposal of the disposable. Furthermore, batteries or rechargeable batteries have a limited durability on a longer storage or time of use.

A plurality of sensors and/or transmitters and/or energy converters can be present in the disposable article. It is preferred that every sensor is in connection, for example cable connection, with a transmitter and an energy converter within the disposable or forms a construction unit therewith. It is further preferred that every transmitter is in connection, for example cable connection, with an energy converter within the disposable or forms a construction unit therewith.

In an embodiment, the energy converter is a thermoelectric energy converter and preferably a Peltier element. A thermoelectric element utilizes a temperature difference, for example the temperature difference between the blood or dialysate flowing or located in the dispensable part and the environment, for example while utilizing the Seebeck effect, to generate electrical energy. Such elements can be miniaturized and are simple and inexpensive to manufacture.

In an embodiment, the energy converter is configured to convert kinematic or mechanical energy into electrical energy. Such energy converters can, for example, be configured to generate electrical energy on the basis of pressure changers or movements, e.g. pulsation generated by a pump, optionally a peristaltic pump, or movement of the blood or dialysate flowing or located in the disposable part.

In an embodiment, the energy converter is configured to receive electromagnetic energy and to convert it into electrical energy. Electromagnetic energy can be transmitted wirelessly. For example, a transmitter for electromagnetic energy can be present which is then converted into electrical energy at the disposable by the corresponding energy converter.

A plurality of different kinds of energy converters can also be used at a disposable part in accordance with the invention.

In an embodiment, the sensor is a pressure sensor, a temperature sensor, a flow sensor or a conductivity sensor. Further sensors are naturally also conceivable which are suitable for determining a state variable or a parameter of the dialysate or blood. Such sensors are preferably used which can be operated with electrical energy and have a low energy consumption. Examples comprise a capacitive pressure sensor or a resistance thermometer. A plurality of different kinds of sensors can also be used at a disposable part in accordance with the invention.

In an embodiment, the disposable article is an extracorporeal blood circuit for hemodialysis which preferably comprises a blood line having an arterial line and a venous line, a dialyzer and a dialysate line. Within the framework of the present invention, the term hemodialysis is used as an umbrella term which covers the hemodialysis in the narrower sense, hemodiafiltration and hemofiltration. The blood line and the dialysate line can be configured as hose lines, for example. Furthermore, a cassette system is conceivable, wherein the blood line and the dialysate line are configured as channels in the cassette. The disposable can furthermore have catheters for connecting the arterial line and the venous line to the patient.

The or one sensor in the extracorporeal blood circuit configured as a disposable in accordance with the invention can be arranged at one or more of the following sites, for example:

in the arterial line of the extracorporeal blood circuit;
in the venous line of the extracorporeal blood circuit;
upstream of the dialyzer in the dialysate line;
downstream of the dialyzer in the dialysate line;
on the blood side of the dialyzer, optionally at the inlet side or at the outlet side; or
on the dialysate side of the dialyzer, optionally at the inlet side or at the outlet side.

In an embodiment, a pressure sensor is arranged in the venous line of the extracorporeal blood circuit. A monitoring of the venous pressure at the venous catheter can thereby be achieved. An advantage in this embodiment is the accurate monitoring by a measurement directly at the blood, the lack of disturbing cables and the lack of relevance of the distance between the patient and the dialyzer.

In an embodiment, a thermoelectric energy converter is arranged in the venous line of the extracorporeal blood circuit and preferably close to the catheter. The body heat of the patient can thus be used for energy harvesting.

In an embodiment, at least two pressure sensors are arranged in the extracorporeal blood circuit so that the transmembrane pressure can be measured at the dialyzer. A conceivable arrangement in this connection comprises the presence of pressure sensors on the dialysate side and on the blood side of the dialysis machine, optionally at one side or respectively at the inlet side and the outlet side. A further conceivable arrangement comprises the presence of pressure sensors upstream and/or downstream of the dialysis machine in the arterial blood line and/or venous blood line as well as in the dialysate line.

In an embodiment, at least two pressure sensors are arranged in the longitudinal direction at the dialysis machine so that the pressure development can be measured in the longitudinal direction of the dialysis machine. This optionally allows a gradient of the dialysis affectivity.

In an embodiment, one or more temperature sensors are located in the dialysate line, in the blood line and/or in the dialysis machine. The temperature can thus be accurately monitored. An arrangement of the temperature is preferred, for example, on the dialysate side and optionally furthermore on the blood side of the dialyzer. The heat input into the blood can thus be determined directly at the dialyzer and no falsification takes place by possible temperature losses at the hose. This can be utilized for improvements in temperature management at the dialyzer. The total energy balance can be recorded directly at the dialyzer so that the thermal efficiency of the heat exchanger dialyzer can be determined without systematic measurement errors.

In an embodiment, the disposable article is a container for a dialysate or a concentrate for manufacturing a dialysate. The disposable article in this embodiment can therefore, for example, be a storage container to be connected to a dialysis machine.

In an embodiment, the sensor is a filling level sensor. The filling level can be accurately determined with the aid of a filling level sensor arranged directly at the container formed as a disposable. The filling level sensor can be configured, for example, so that the filling level is determined via a pressure measurement or via a conductivity measurement.

Alternatively or additionally, a conductivity sensor is also conceivable at such a container, for example for determining the composition of the dialysate or of the concentrate. A temperature sensor is furthermore also conceivable. It can be arranged in the bag and can serve the determination of the temperature on a heat sterilization of the dialysate or concentrate or on a cleaning of the container. It can also be arranged in an outflow line belonging to the bag to determine the temperature of the dialysate.

The invention further relates to a dialyzer having a disposable article in accordance with the invention. This dialyzer can, for example, have a receiver for signals from transmitters arranged in the disposable article. Furthermore, it can, for example, have a radiation source for outputting electromagnetic energy to an energy converter for electromagnetic energy arranged in the disposable article.

The case is furthermore also covered by the invention in which the autonomous measurement unit comprising the sensor, transmitter and energy converter is arranged at the machine side.

The invention accordingly relates to a dialyzer having at least one sensor for determining at least one measured value relating to the dialysis, at least one transmitter which allows a wireless transmission of the measured value to at least one receiver and at least one energy converter for providing energy, preferably electrical energy to the sensor and to the transmitter.

It is also advantageous at the machine side to transfer the measured signal to a receiver via radio and to allow an autonomous operation of the sensor at any desired sites in the unit, whereby inter alia the necessity to install some cables is dispensed with.

The energy converter and/or the sensor can in this respect be configured and can be in communication with one another in different embodiments such as was described above in connection with the disposable in accordance with the invention.

In an embodiment, the dialyzer has a hydraulic system for conveying dialysate and the sensor is arranged at a point of this hydraulic system. The concept of the autonomous measured data detection can be transmitted in this connection to any measured site in the hydraulics at the machine side. Optionally, furthermore, the energy converter is also arranged at one point or at this point of the hydraulic system. It can, for example, utilize the fluid flow or the increased temperature in the hydraulic system for energy harvesting. The transmitter can furthermore also be arranged at one point or at this point in the hydraulic system. The transmitter can, however, also be arranged outside the hydraulic system and can be in communication with the sensor and the transmitter. The positional designation "at the" hydraulic system designates such a contact with fluid or actuators of the hydraulic system that measured data can be detected by this contact or that energy can be harvested by this contact. The positional designation "outside" the hydraulic system designates a lack of such a contact.

In an embodiment, the dialyzer has a water preparation plant for the dialysate manufacture and the sensor is arranged at a point of this water preparation plant. It is furthermore conceivable that the dialyzer has a water preparation plant for the dialysate manufacture or is in communication with same and the sensor is arranged at this point of this water preparation plant.

The invention furthermore also relates in this connection, considered in isolation, to a water preparation plant for the dialysate manufacture having at least one sensor for determining at least one measured value relating to the dialysis, at least one transmitter which allows a wireless transmission of the measured value to at least one receiver and at least one energy converter for providing energy, preferably electrical energy to the sensor and to the transmitter.

The energy converter and/or the sensor can in this respect be configured and can be in communication with one another in different embodiments such as was described above in connection with the disposable in accordance with the invention.

In dialysis technology, water preparation plants are used for the dialysate manufacture. An autonomous system can, for example, be used for the temperature monitoring during a heating sterilization carried out regularly in such systems.

The sensor is arranged at a point of the water-conducting system of this water preparation system. Optionally, furthermore, the energy converter is also arranged at one point or at this point of the hydraulic system. It can, for example, utilize the increased temperature during the heat sterilization for energy harvesting.

Figure 2:
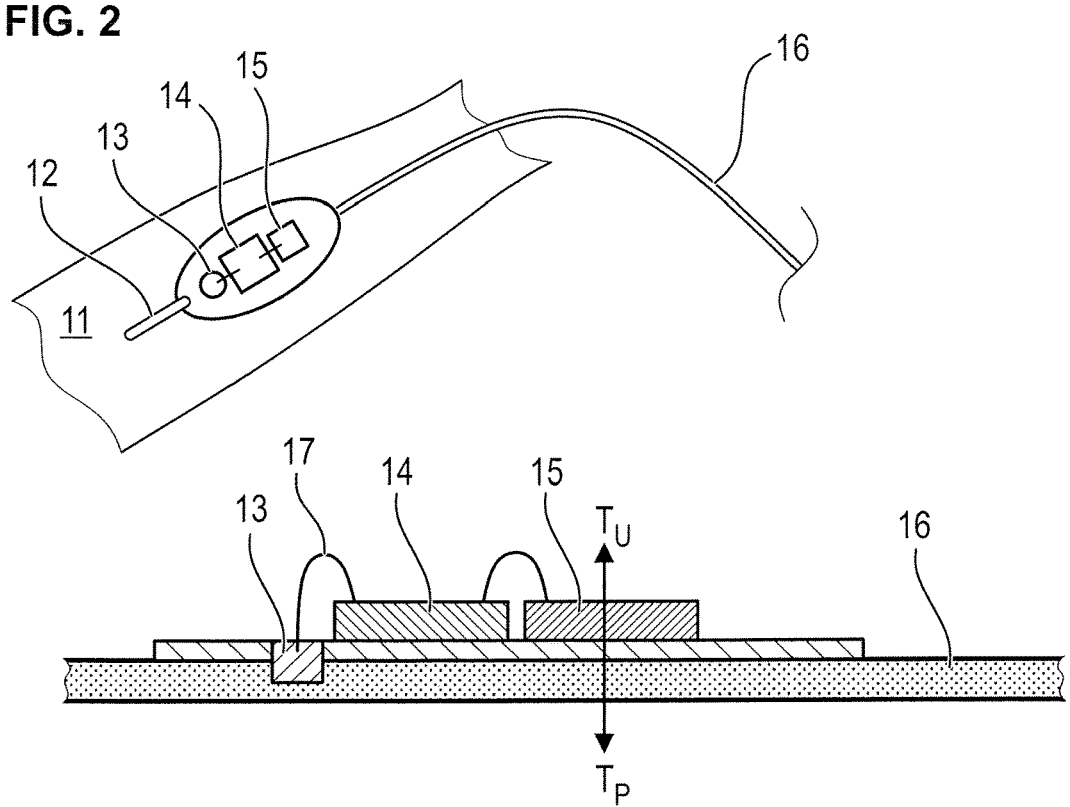
Figure 3:
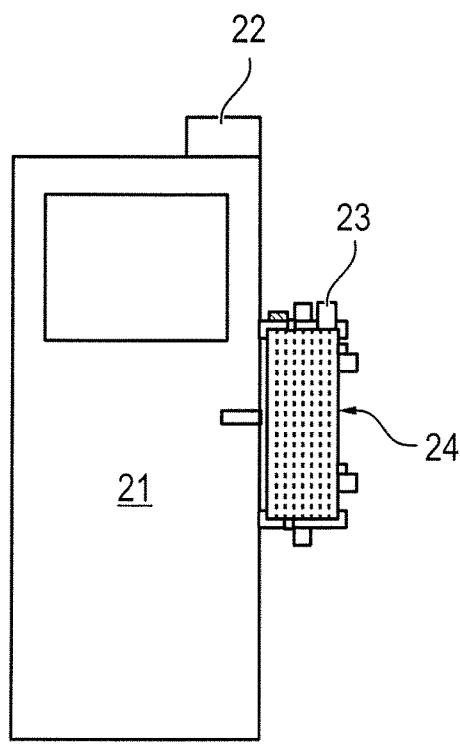
Figure 4:
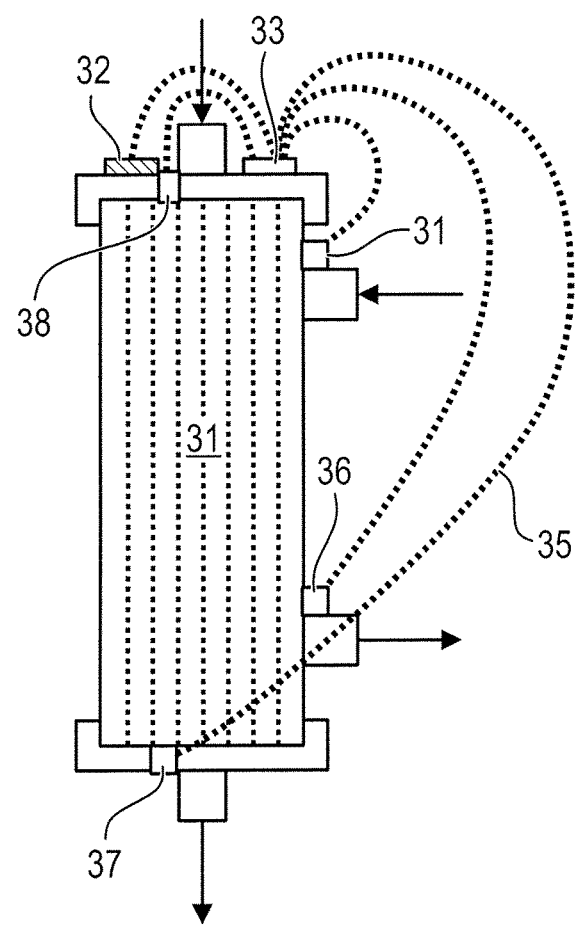
Figure 5:
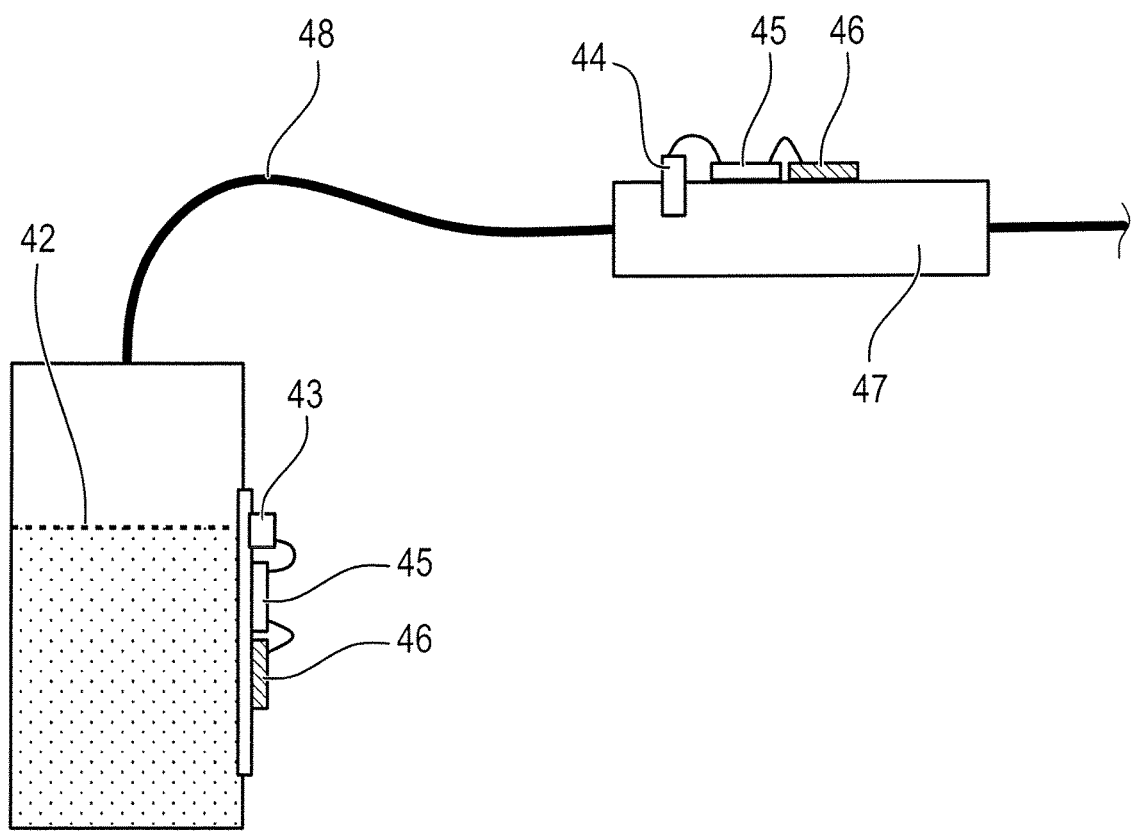
Figure 6:
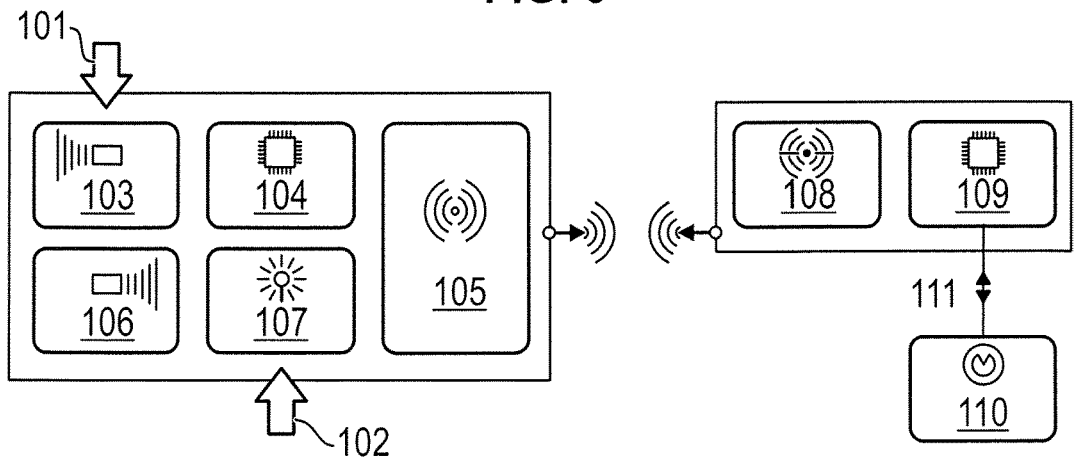
Figure 7:
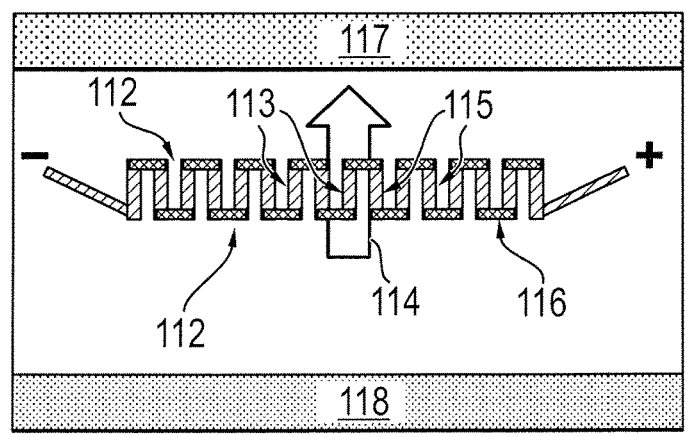
Figure 8:
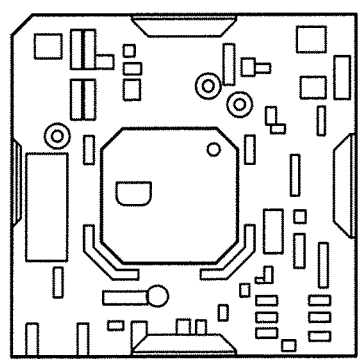

Further details and advantages results from the Figures and embodiments discussed in the following. There are shown in the Figures:

FIG. 1: a representation of the measurement of the venous blood pressure directly at the vessel access using a disposable in accordance with the invention;

FIG. 2: a plan view and a sectional representation of the measurement of the venous blood pressure directly at the vessel access using a disposable in accordance with the invention;

FIG. 3: a representation of the measurement of the pressure and temperature directly at the dialyzer of a disposable in accordance with the invention;

FIG. 4: a detailed view of the dialyzer of FIG. 3 at the disposable side;

FIG. 5: a representation of the measurement of the filling level and temperature directly at a disposable container for dialysate;

FIG. 6: a schematic representation of the measurement, energy conversion and radio technology for use in a disposable in accordance with the invention;

FIG. 7: a representation of the energy conversion for use in a disposable in accordance with the invention; and FIG. 8: an image of a thermoelectric energy converter for use in a disposable in accordance with the invention.

EMBODIMENT 1

Measuring the Venous Blood Pressure Directly at the Vessel Access

The blood pressure should be able to be measured directly at the venous catheter at the disposable side.

The sensor is arranged directly at the venous catheter of the extracorporeal blood circuit configured as a disposable and comprising a blood line having an arterial line and a venous line, a dialyzer and a dialysate line. This can be recognized in FIGS. 1 and 2.

In the representation in accordance with FIG. 1, reference numeral 1 shows the patient on whom a dialysis treatment is being carried out. A transmitter 2 is located at the venous blood return line 3 for the wireless transmission of data to the reception unit 4 which is arranged internally or externally at the dialysis machine 5.

In FIG. 2, the part of the disposable located close to the patient in such an arrangement is shown in greater detail, and indeed in a plan view at the top left in the Figure and in a sectional representation at the bottom right in the Figure. The arm of the patient is shown by the reference numeral 11. The venous blood return line 16 is in communication with the bloodstream of the patient 11 by way of the vessel access 12. The vessel access 12 can, for example, be a needle or a catheter. A pressure sensor 13 is arranged directly at the vessel access 12 at the disposable side and measures the absolute pressure $P_{venous}$ of the blood in the venous return line 16 directly before the return to the patient 11. A thermoelectric Peltier element is designated by reference numeral 15 and utilizes the temperature difference between the environmental temperature $T_U$ (for example 20° C.) and the body temperature of the patient $T_P$ (37° C.) for generating electrical energy. A transmission unit is designated by reference numeral 14 which transfers the measured data of the pressure sensor 13 to a receiver 4 arranged at the machine side. The transmitter 14, the pressure sensor 13 and the thermoelectric energy converter 15 are in communication via electrical connections 17. The transmitter 14 and the pressure sensor 13 are supplied with electrical energy by the energy converter 15 by way of these electrical connections 17. The measured data of the pressure sensor 13 furthermore arrive at the transmitter 14 by way of these electrical connections 17. Both the pressure sensor 13 and the transmitter 14 and the energy converter 15 are parts of the disposable.

The capacitive pressure sensor SCB10H of the VTI company which has a very low energy consumption is used as the sensor. Other suitable pressure sensors can naturally also be used.

The arrangement of the sensor directly at the venous catheter has the advantages of a very short response time on disconnection of the venous needle and of a lack of influence on the measured variable by the hose line or by changes in the hose position.

The wireless transmitter STM 312 (868 MHz) of the Enocean company, which is likewise arranged at the disposable, is used as the transmitter for the data of the sensor. Alternatively, for example, the wireless transmitter STM 312C (868 MHz) or ETC 310 of the Enocean company could also be used. A standard Peltier element in combination with EnOcean Ultra Low Power DC/DC converter serves as an energy source for the sensor and the transmitter which serves as a power source utilizing the Seebeck effect and the temperature difference between the blood (as a rule >35° C.) and the environment (as a rule <25° C.). No external energy supply or sensor line is therefore required since a temperature difference typical for dialysis is utilized as the energy source. Other suitable wireless transmitters and energy sources can naturally also be used.

The shown type of attachment of the sensor, of the transmitter and of the energy converter at the disposable part also has the advantage among others of no cables at the needle so that no mechanical impairment or danger for the access and no impairment for the freedom of movement of the patient arise. The embodiment of the sensor as a disposable moreover brings about hygienic advantages. Due to the design of the energy source as a thermoelectric energy converter, the measurement only starts when the disposable is put into operation. No switching on is necessary and no permanent transmission of the transmitter takes place. A battery or similar is not necessary, which has a positive effect on the storage time of the disposable which could be limited under certain circumstances by the service life of a battery.

The sensor system can be completely cast or injection molded so that a hermetic seal against moisture is present.

The functional principle of the energy harvesting used in a thermal energy converter while utilizing the temperature difference typical for dialysis between the dialysate or blood and the environment is shown schematically in FIG. 7. The position of the 37° C. hot blood or dialysate is schematically indicated by reference numeral 118 and the environment, which is approximately 20° C. hot, is indicated by reference numeral 117. Reference numerals 113 show p conductors and reference numerals 115 n conductors. A heat stream is symbolized by reference numeral 114. Reference numeral 116 shows metallic bridges between the p conductors 113 and the n conductors 115. Reference numeral 112 shows an electrical insulation above or below the metallic bridges 116 and semiconductors 113 and 115.

If thermal energy is taken up at the contact point between the n conductor 115 and the p conductor 113, electrons can thereby move from the n conductor 115 into the energetically higher conduction band of the adjacent p conductor 113. A current flow therefore takes place from the p-doped semiconductor to the n-doped semiconductor.

FIG. 8 shows an image of a thermal energy converter.

A schematic outline of the measurement of data, energy conversion and transmission of data for use in a disposable in accordance with the invention is shown in FIG. 6.

The left hand representation shows a sensor radio module which is arranged at the disposable side. It comprises a sensor system 106 for detecting measured data 102, a processor 104 for measured data processing, an energy converter 103 for harvesting electrical energy from thermal energy 101, for example, an electronic system 106 for energy management and an HF transceiver 105 as the transmitter.

The right side shows a system radio module arranged at the machine side. It comprises an HF transceiver 108 as a receiver for the radio signals of the transmitter 105 and a processor 109 for the data processing. Reference numeral 110 shows an actuator of the device which can be controlled by the device control in dependence on the received measured signal and on the evaluated data. In this respect, it is, for example, a pump, a heating or similar. The transmission and conversion of the measured signal into a control signal is symbolized by reference numeral 111.

EMBODIMENT 2

Measuring the Variables Pressure and Temperature at the Dialyzer

The measured variables of the dialyzer inlet pressure and of the dialyzer outlet pressure important for the treatment can be measured at the disposable side. The disposable comprises a blood line having an arterial line and a venous line, a dialyzer and a dialysate line.

For this purpose, pressure sensors are arranged directly at the inlet and outlet points at the dialyzer of the disposable both at the blood side and at the dialysate side. Capacitive pressure sensors SCB110H of the VTI company which have a very low energy consumption are used as the pressure sensors. Other suitable sensors can naturally also be used.

The transmembrane pressure can thus be determined directly and precisely at the dialyzer. No influencing of the measured variables by the hose line takes place (pressure drops at the hose); a direct monitoring of the pressure drops typical for a dialyzer takes place, inter alia axial pressure drop, over the fibers; and a fast and early clotting recognition is possible.

Furthermore, the temperature of the dialysis should be measured at the dialyzer. The jacket resistance thermometer PT1000 is arranged at the dialyzer at the disposable side. Other suitable sensors can naturally also be used. The heat input into the blood can thus be determined directly at the dialyzer and no temperature loss takes place at the hose, for example. This can be utilized for improvements in temperature management at the dialyzer. The total energy balance can be recorded directly at the dialyzer so that the thermal efficiency of the heat exchanger dialyzer can be determined without systematic measurement errors.

Such a system for measured data detection at the disposable side and for wireless measured data transfer is shown in FIGS. 3 and 4.

In the representation in accordance with FIG. 3, reference numeral 21 shows a dialysis machine at which the reception unit 22 is arranged internally or externally. Reference numeral 24 symbolizes the dialyzer which has a plurality of measuring cells, an energy converter and a transmitter 23 for wireless transmission of data to the reception unit 22.

The dialyzer 24 and 31 respectively of the disposable is shown in greater detail in such an arrangement in FIG. 4. As can be seen from this, it is in this respect a typical hollow fiber dialyzer, wherein blood flows from the top to the bottom in the Figure through the interior of the hollow fibers, and wherein the hollow fibers in the dialyzer chamber are flowed around by dialysate flowing into the dialyzer chambers from the side and flowing out of the dialyzer chamber from the side. The dialyzer can naturally also be operated in the counter-flow principle, which is even preferred.

A plurality of sensors are located at the dialyzer:

A pressure sensor and a temperature sensor (shown in combination as sensor 34) on the dialysate side at the inlet of the dialyzer;

A pressure sensor and a temperature sensor (shown in combination as sensor 36) on the dialysate side at the outlet of the dialyzer;

A pressure sensor and a temperature sensor (shown in combination as sensor 37) on the blood side at the outlet of the dialyzer;

A pressure sensor and a temperature sensor (shown in combination as sensor 38) on the dialysate side at the inlet of the dialyzer;

A thermoelectric Peltier element is designated by reference numeral 32 which utilizes the temperature difference between the environmental temperature, for example 20° C., and the blood temperature or dialysate temperature at the dialyzer, as a rule 37° C., for generating electrical energy.

A transmission unit is designated by reference numeral 33 which transmits the measured data of the sensors 34, 36, 37 and 38 to a receiver 22 arranged at the machine side. The transmitter 33, the sensors 34, 36, 37 and 38 and the thermoelectric energy converter 32 are in communication via electrical connections 35. The transmitter 33 and the sensors 34, 36, 37 and 38 are supplied with electrical energy by the energy converter 32 by way of these electrical connections 35. The measured data of the sensors 34, 36, 37 and 38 furthermore arrive at the transmitter 33 by way of these electrical connections 35. Both the sensors 34, 36, 37 and 38 and the transmitter 33 and the energy converter 32 are parts of the disposable.

The wireless transmitter is used as the transmitter for the data of the sensors which is likewise arranged at the disposable and which was already described in connection with embodiment 1. A standard Peltier element having a DC/DC converter such as was already described in connection with embodiment 1 serves as an energy source for sensors and transmitters. The temperature difference between the dialysate (as a rule >35° C.) and the environment (as a rule <25° C.) is utilized. Other suitable wireless transmitters and energy sources can naturally also be used.

In this embodiment, no cables are located at the dialyzer so that no impairment of the freedom of movement of the patient arises. Hygienic advantages arise due to the design of the sensors as a disposable. No external energy supply or sensor lines are therefore required since a temperature difference typical for dialysis is utilized as the energy source. The measurement only starts when the disposable is taken into operation. No switching on is necessary and no permanent transmission of the transmission unit takes place. A battery or similar is not necessary, which has a positive effect on the storage time of the disposable which could be limited under certain circumstances by the service life of a battery. The sensor system can be completely cast or injection molded so that a hermetic seal against moisture is present.

In summary, therefore, a plurality of advantages can be achieved in the embodiments by the arrangement of a thermal generator at the disposable side at the dialyzer, by the pressure measurement in the dialysate and/or blood and by a cableless data transmission. This inter alia includes the lack of a disturbing disposable between the sensor and the measuring medium. The invention therefore provides an intelligent battery-less disposable within the framework of this embodiment.

EMBODIMENT 3

Measuring the Filling Level and the Temperature Directly at a Disposable Container for Dialysate FIG. 5 shows a schematic representation of the measurement of the filling level and the temperature at a disposable container using sensors, energy converters and wireless transmitters arranged at the disposable side.

In this FIG. 2, the disposable container 41 is shown at the bottom left and the hose 48, likewise belonging to the disposable, at the top right.

A level sensor which is arranged at the disposable side and which detects the filling level 42 of the container is designated by the reference numeral 43. A temperature sensor 44 (PT1000) arranged at the disposable side is shown by the reference numeral 44 which detects the temperature of the dialysate using two spouts in the smaller chamber 47 which is arranged at the hose line 48. The disposable can naturally also only comprise the filling level sensor 43 or the temperature sensor 44.

Thermoelectric Peltier elements are designated by reference numeral 46 which utilize the temperature difference between the environmental temperature (for example 20° C.) and the temperature of the dialysate (typically 37° C.) to generate electrical energy.

Transmission units are designed by reference numerals 45 which transmit the measured data 43 and/or 44 to a receiver arranged at the machine side.

The transmitters 45, the sensors 43 and/or 44 and the thermoelectric energy converters 46 are in communication so that a transmitter 45 and a sensor 43 or 44 are supplied with electrical energy from an associated energy converter 46. Furthermore, the measured data of a respective sensor 43 or 44 arrive at the respective transmitter 45. Both the sensors 43 and/or 44 and the transmitters 45 and the energy converters 46 are parts of the disposable.

The components explained in connection with embodiment 1 are used as the transmitters and energy converters.

EMBODIMENT 4

Measuring the Level and/or Pressure and/or Conductivity and/or Temperature in the Hydraulic System In this embodiment, a thermal generator is arranged at the hydraulic system at the machine side. A measured value detection takes place at the hydraulic system by a sensor which is energy-autonomous due to the thermal generator and a cableless data transmission takes place by a transmitter which is energy-autonomous due to the thermal generator and which is connected to the sensor. This concept of measured data detection can essentially be used at any measuring site and for any desired measured value in the hydraulic system.

The advantages include the lack of a need for cables or a battery. The autonomous measuring unit is space-saving, simple to assemble and can be easily serviced.

The components explained in connection with embodiment 1 are used as the transmitters and energy converters in the embodiment.

EMBODIMENT 5

Measuring the Level and/or Pressure and/or Conductivity and/or Temperature in a Water Preparation Plant for Permeate In this embodiment, a thermal generator is arranged at the water preparation plant for permeate at the machine side, for example at a pipeline of the water preparation plant. A measured value detection takes place by a sensor which is energy-autonomous due to the thermal generator and a cableless data transmission takes place by a transmitter which is energy-autonomous due to the thermal generator and which is connected to the sensor.

In dialysis technology, water preparation plants are used for the permeate manufacture. These systems are being subjected more and more frequently to disinfection/cleaning with hot water. In this respect, proof has to be provided that the temperature required for a cleaning is achieved in all regions of the pipeline system. In this respect, the positions in outwardly disposed regions of the system are relevant to a particular degree. The spatial distance between the measuring point and the evaluation unit (dialyzer/RO plant) is thus frequently large. The autonomous measuring unit is therefore particularly advantageous.

The temperature difference between the pipeline/machine part and the environment is large during the thermal disinfection. The energy harvesting with the aid of the thermal generator is therefore particularly efficient.

The components explained in connection with embodiment 1 are used as the transmitters and energy converters in the embodiment.

The invention claimed is:

1. A disposable extracorporeal blood circuit, for use in hemodialysis, comprising
    a venous line,
    a support extending along the venous line,
    at least one pressure measuring sensor coupled to the support and extending through the support into the venous line,
    at least one energy converter coupled to the support for providing electrical energy, and
    at least one transmitter coupled to the support and electrically connected to the pressure sensor and the energy converter for wireless transmission and reception outside the disposable extracorporeal blood circuit of pressure measured by the at least one pressure measuring sensor.

2. The disposable extracorporeal blood circuit in accordance with claim 1, characterized in that the at least one energy converter is a thermoelectric energy converter.

3. The disposable extracorporeal blood circuit in accordance with claim 1, characterized in that the at least one energy converter is a Peltier element.

4. The disposable extracorporeal blood circuit in accordance with claim 1, characterized in that the at least one energy converter converts kinematic or mechanical energy into electrical energy.

5. The disposable extracorporeal blood circuit in accordance with claim 1, characterized in that the at least one energy converter converts electromagnetic energy into electrical energy.

6. The disposable extracorporeal blood circuit in accordance with claim 1, characterized in that the at least one energy converter is a thermoelectric energy converter arranged in the venous line.

7. The disposable extracorporeal blood circuit in accordance with claim 1 further comprising an arterial line.

8. The disposable extracorporeal blood circuit in accordance with claim 7, characterized in that the at least one energy converter is a thermoelectric energy converter.

9. The disposable extracorporeal blood circuit in accordance with claim 7, characterized in that the at least one energy converter is a Peltier element.

10. The disposable extracorporeal blood circuit in accordance with claim 7, characterized in that the at least one energy converter converts kinematic or mechanical energy into electrical energy.

11. The disposable extracorporeal blood circuit in accordance with claim 7, characterized in that the at least one energy converter converts electromagnetic energy into electrical energy.

12. The disposable extracorporeal blood circuit in accordance with claim 7, characterized in that the at least one energy converter is a thermoelectric energy converter arranged in the venous line.

* * * * *